(12) United States Patent
Lim et al.

(10) Patent No.: US 8,940,311 B2
(45) Date of Patent: Jan. 27, 2015

(54) IN SITU CONTROLLED RELEASE DRUG DELIVERY SYSTEM

(75) Inventors: Tae-Hong Lim, Coralville, IA (US); Joon B. Park, Coralville, IA (US); Jin Whan Lee, Coralville, IA (US)

(73) Assignee: Tae-Hong Lim, Coralville, IA (US)

( * ) Notice: Subject to any disclaimer, the term of this patent is extended or adjusted under 35 U.S.C. 154(b) by 2606 days.

(21) Appl. No.: 11/256,416

(22) Filed: Oct. 21, 2005

(65) Prior Publication Data

US 2006/0188583 A1 Aug. 24, 2006

Related U.S. Application Data

(60) Provisional application No. 60/620,929, filed on Oct. 21, 2004.

(51) Int. Cl.
| | | |
|---|---|---|
| A61K 9/00 | (2006.01) | |
| A61K 9/50 | (2006.01) | |
| A61K 9/16 | (2006.01) | |
| A61K 47/34 | (2006.01) | |

(52) U.S. Cl.
CPC ............ *A61K 9/5031* (2013.01); *A61K 9/0024* (2013.01); *A61K 9/1647* (2013.01); *A61K 9/5084* (2013.01); *A61K 47/34* (2013.01)
USPC .......................................... 424/400; 424/489

(58) Field of Classification Search
None
See application file for complete search history.

(56) References Cited

U.S. PATENT DOCUMENTS

| | | | |
|---|---|---|---|
| 4,389,330 A | 6/1983 | Tice et al. | |
| 6,287,588 B1 | 9/2001 | Shih et al. | |
| 6,426,332 B1 | 7/2002 | Rueger et al. | |
| 6,589,549 B2* | 7/2003 | Shih et al. | 424/426 |
| 7,582,311 B1 | 9/2009 | Cleland et al. | |
| 2001/0036943 A1* | 11/2001 | Coe et al. | 514/220 |
| 2001/0049518 A1* | 12/2001 | Hoch | 604/510 |
| 2006/0235114 A1 | 10/2006 | Kitazono et al. | |

FOREIGN PATENT DOCUMENTS

| | | |
|---|---|---|
| KR | 0146386 | 5/1998 |
| WO | 9503036 A1 | 2/1995 |
| WO | WO99/07343 | 2/1999 |
| WO | 0000222 A1 | 1/2000 |
| WO | WO 03/043576 A2 | 5/2003 |
| WO | 03061690 A1 | 7/2003 |

OTHER PUBLICATIONS

Jameela, S.R., et al., "Protein release from polcaprolactone microspheres prepared by . . . ", 1997, 8(6), pp. 457-466.*
Kim, RK., et al., "Temperature-responsive and degradable hyaluronic acid/pluronic . . . ", 2002, Journal of Controlled Release, 80, pp. 69-77.*
Cortesi, Rita et al., "Production of liposheres as carriers for bioactive compounds", (2002) Biomaterials 23, pp. 2283-2294.
Jameela, S. R., et al., "Protein release from poly(Epsilon-caprolactone) microspheres prepared by melt encapsulation and solvent evaporation techniques: A comparative study", (1997), J. Biomater. Sci. Polymer Edn., vol. 8, No. 6, pp. 457-466.
Lin, W.J. et al., "Comparison of protein loaded poly(Epsilon-caprolactone) microparticles prepared by the hot-melt technician", 2001, J. Microencapsulation, vol. 18, No. 5, pp. 585-592.
Lin, W.J. et al., "Comparison of chitosan and gelatin coated microparticles: prepared by hot-melt method", 2003, J. Microencapsulation, vol. 20, No. 2, pp. 169-177.
Reithmeier, Helmut et al., "Lipid microparticles as a parenteral controlled release device for peptides", 2001 Journal of Controlled Release, 73, pp. 339-350.
European Search Report, completed May 15, 2012, mailed Jun. 1, 2012, Applicant: University of Iowa Research Foundation, Application No. 05815217.4-2112/1807018, PCT/US2005/037872 filed on Oct. 21, 2005 (7 pages).

* cited by examiner

*Primary Examiner* — Michael G Hartley
*Assistant Examiner* — Lance Rider
(74) *Attorney, Agent, or Firm* — McKee, Voorhees & Sease

(57) ABSTRACT

A system is described for long-term controlled release delivery of a drug or a therapeutic agent. According to the invention, one or more drugs or therapeutic agents contained in microspheres are mixed with a temperature sensitive hydrogel which is then introduced directly to the desired situs of the drug or therapeutic agent. The temperature sensitive hydrogel may also contain a drug or a therapeutic agent, for example, a pain relieving drug, for a short-term controlled release. The temperature sensitive hydrogel is in liquid state at room temperature, but upon injection, shortly becomes gelatinous. This system is particularly suitable for treatment of diseases, disorders, or conditions, for example, tumors, discogenic back pain, or arthritis, warranting localized administration of a drug or a therapeutic agent. In addition, the specification provides a method for production of a drug- or therapeutic agent-containing microspheres.

20 Claims, 14 Drawing Sheets

Mean±SD:
4.77±1.49 μm

IN SITU CONTROLLED RELEASE DRUG DELIVERY SYSTEM

FIELD OF THE INVENTION

The present invention relates to temperature sensitive compositions for controlled drug delivery and methods for administering a drug or therapeutic agent via these compositions to a specific site in a subject.

BACKGROUND OF THE INVENTION

Targeted therapeutic delivery means are particularly important where the toxicity of a drug is an issue. Specific therapeutic delivery methods potentially serve to minimize toxic side effects, lower the required dosage amounts, and decrease costs for the patient. The present invention is directed to addressing these and/or other important needs in the area of drug and therapeutic delivery.

Rapid advances in the fields of pharmaceutics, genetic engineering and biotechnology have led to the development of an increasing number of drugs and therapeutic agents. The development of methods for administering these new pharmaceutical agents is thus becoming increasingly important.

Many drugs and therapeutic agents have relatively short half-lives, requiring frequent administration to achieve efficacious levels. To increase patient convenience and to improve efficacy, controlled release compositions of drugs and therapeutic agents are highly desirable. Despite the advances provided by the available polymers and hydrogels, the delivery of a drug or therapeutic agent to a patient has largely been systemic and rapid, in some cases not allowing the desired result to be achieved. Therefore, there is a need in the art for means for the localized delivery of a drug or therapeutic agent to a subject, particularly in a controlled-release manner.

It is therefore an objective of the present invention to provide site-specific delivery of a drug or therapeutic agent to an animal.

It is another objective of the present invention to provide controlled release of a drug or therapeutic agent to an animal.

It is another objective of the present invention to localize a drug or therapeutic agent to a specific site in an animal.

It is still another objective of the present invention to deliver a drug or therapeutic agent to an animal for the treatment of a disease, disorder or condition.

These and other objectives will become apparent from the following description.

SUMMARY OF THE INVENTION

The invention allows for the controlled delivery of a drug or therapeutic agent through the use of a temperature sensitive hydrogel and microspheres of biocompatible polymers. The use of this system to treat a mammal has the advantage of requiring less frequent administration of the drug or therapeutic agent and avoidance of surgical intervention. Thus, the invention comprises a system, method, and pharmaceutical composition suitable for short or long-term effectiveness or treatment.

According to the invention, microspheres made of a biocompatible polymer are generated which contain a drug or therapeutic agent. These microspheres are mixed and suspended within a temperature sensitive hydrogel. At room temperature, the hydrogel is in liquid phase. Soon after injection into a subject, the liquid hydrogel becomes a gel due to body temperature. The drugs or therapeutic agents contained in the microspheres will diffuse into the subject's extracellular matrix, and will be released to the targeted site in a controlled manner.

The invention includes a pharmaceutical composition for controlled drug release comprising a plurality of drug or therapeutic agent containing biodegradable and biocompatible polymer microspheres, wherein the microspheres are suspended within a temperature sensitive hydrogel. Methods of treating diseases, disorders, or conditions which include introducing this system to a patient in need of a drug or therapeutic agent as well as methods of making the system of the invention are disclosed.

The in-situ gelling system according to the invention can deliver the drug or therapeutic agent directly to the target, such as a painful interverterbral disc or tumor, and provide short or long-term treatment by the controlled release of the drug or therapeutic agent in the target area. The system is applied to the targeted area for delivery of the drug or therapeutic agent. Application of the system may be by any means necessary to introduce the drug or therapeutic agent in vivo to the mammal including invasive surgery and/or application, preferentially, by injection to the situs. The in-situ gelling system of the invention may also be adapted for use in other treatments.

DETAILED DESCRIPTION OF THE PREFERRED EMBODIMENT

Figure 1:
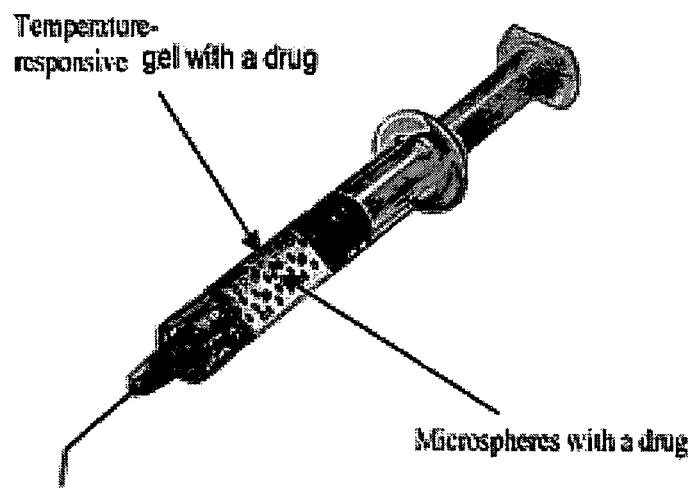
FIG. 1 is a plan view of a syringe prepared according to the system of the current invention. It shows microspheres containing a pain relieving drug mixed with a temperature sensitive hydrogel prepared for percutaneous injection into the painful site of the body.

The present invention provides methods and compositions for the site-specific delivery of a drug or therapeutic agent included in a microsphere-hydrogel mixture. These methods and compositions provide for the delivery of these compositions with sustained and/or controlled release for the treatment of a variety of diseases, disorders, and conditions, including without limitation, viral, yeast, and bacterial infections, cancer, inflammation, autoimmune diseases, joint and back injuries, and arthritis.

DEFINITIONS

As used herein, the term "biocompatible" is used herein to mean material that interacts with the body without undesirable aftereffects.

As also used herein, the term "microspheres" refers to a spherical particle formed of polymers.

As used herein, the term "biodegradable" refers to materials which are enzymatically or chemically or otherwise degraded in vivo into simpler chemical species.

As used herein, the term "sustained release" refers to the continual release of a drug or therapeutic agent or any combination thereof over a period of time.

As used herein, the term "controlled release" refers to control of the rate and/or quantity of a drug or therapeutic agent delivered according to the drug delivery formulations of the invention. The controlled release can be continuous or discontinuous, and/or linear or non-linear. This can be accomplished using one or more types of polymer compositions, drug loadings, inclusion of excipients or degradation enhancers, or other modifiers, administered alone, in combination or sequentially to produce the desired effect.

As used herein, the term "drug" means a substance intended for use in the diagnosis, characterization, cure, mitigation, treatment, prevention or allaying the onset of a disease, disorder, or other condition in humans and/or in non-human animals.

As used herein, the term "therapeutic agent" refers to any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. The term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, $\beta$-blockers, $\beta$-agonists and antiarrythmics); antihypertensives; chemotherapeutics, diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like).

The present invention provides methods and compositions for the site-specific delivery of a drug or therapeutic agent included in a microsphere-hydrogel mixture. According to the drug delivery system of the present invention, a drug or therapeutic agent can be released in a controlled manner to a targeted site in a subject. In one embodiment, a temperature sensitive hydrogel comprising microspheres is utilized to provide site-specific release of a drug or therapeutic agent to a subject. In another embodiment, the temperature sensitive hydrogel includes at least one drug or therapeutic agent that can be administered to a subject, so that the drug or therapeutic agent is released by diffusion from and/or degradation of the hydrogel. In another embodiment, the hydrogel includes microspheres that contain at least one drug or therapeutic agent that can be administered to a subject, so that the drug or therapeutic agent is released by diffusion from and/or degradation of the microspheres.

As used herein, the term "therapeutic effect" means any improvement in the condition of a subject, human or animal, treated according to the subject method, including obtaining a preventative or prophylactic effect, or any alleviation of the severity of signs and symptoms of a disease, disorder, or condition which can be detected by means of physical examination, laboratory or instrumental methods.

As used herein, unless otherwise defined in conjunction with specific diseases or disorders, the term "treat" or "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

As used herein and in the appended claims, the singular forms "a", "an" and "the" include plural references unless the context clearly dictates otherwise.

In one embodiment of the present invention, a temperature sensitive hydrogel is used to deliver polymer microspheres comprising at least one drug or therapeutic agent.

Polymers are used in preparing the temperature sensitive hydrogels of the present invention. The temperature sensitive hydrogel is designed to be liquid at about ambient room temperature (about 20° C.) and transition to become a solid (gel) at about body temperature (about 37° C.). The polymer used in the preparation of the temperature sensitive hydrogel may be any polymeric material without limitation as long as it possess the necessary properties to support the hydrogel. Examples of polymers that are suitable for preparing a temperature sensitive hydrogel include, but are not limited to, N-isopropyl acrylamide polymer, ethylhydroxyethylcellulose and its derivatives, poly(etheylene oxide-b-propylene oxide-b-ethylene oxide), commonly known as Poloxamers or PLURONICS® polymers, and poly(ethylene glycol)/poly(D,L-lactic acid-co-glycolic acid) block copolymers and analogs thereof. Poloxamers are block copolymers of the type ABA, consisting of a central, hydrophobic block of polypropylene oxide, which is edged by two hydrophilic blocks of polyethylene oxide. The polymers are derived from the sequential polymerization of propylene oxide and ethylene oxide.

In another aspect, the hydrogel may be produced by cross-linking polymers via covalent, ionic, or hydrogen bonds to create a three-dimensional open-lattice structure that entraps water molecules to form a gel. Examples of materials which can be used to form a hydrogel include polysaccharides such as alginate, polyphosphazines, and polyacrylates, which are crosslinked ionically, or block copolymers such as PLURONICS® polymers or TETRONICS® polymers, polyethylene oxide-polypropylene glycol block copolymers which are crosslinked by temperature or pH, respectively. These polymers are either commercially available or can be synthesized using methods known to those skilled in the art. See, for example Concise Encyclopedia of Polymer Science and Polymeric Amines and Ammonium Salts, E. Goethals, editor (Pergamen Press, Elmsford, N.Y. 1980).

Temperature sensitive hydrogels can be prepared using standard techniques routine to one skilled in the art. For example, temperature sensitive hydrogels can be prepared by making polymers or purchasing commercially available polymers, dissolving the polymers in water or other solution and adding to the dissolved polymers, an agent, such as sodium hyaluronate (SH), that facilitates cross-linking of the polymers. See also Examples 2-4. The techniques, amounts, temperature, and time required to produce a hydrogel will be known to those of ordinary skill of the art.

The sensitivity of the hydrogel to various temperatures, e.g. the hydrogel's ability to reversibly transition from a liquid at room temperature to a gel at body temperature, can be determined using standard assays or techniques that measure viscosity and volume change at various temperatures, using for example, a viscometer, described in detail in Examples 2-4 and FIGS. 7-11.

The temperature sensitive hydrogel polymer may also contain at least one drug or therapeutic agent for a short term therapeutic effect or treatment. The drug or therapeutic agent may be added to the polymers used to make the hydrogel prior, during, or after the dissolution of the polymers in solution. Preferably, the drug or therapeutic agent is added prior to the dissolution of the polymer in solution to facilitate a more uniform dispersion or dissolution of the drug or therapeutic agent.

In one aspect of the present invention, the composition includes a temperature sensitive hydrogel mixed with at least one microsphere. In another aspect, the microspheres preferably make up between about 10% and about 50% by volume of the microsphere-hydrogel mixture.

At least one biodegradable polymer is used in the preparation of the microspheres of the present invention. The biodegradable polymer used in the preparation of microspheres may be any polymeric material without limitation as long as it possess the necessary biocompatible and biodegradable properties to support the microsphere, and of course is non-toxic to the mammal. Biodegradable polymers include those of natural and synthetic origins. Examples of natural polymers include proteins such as albumin, collagen, synthetic polyamino acids, and prolamines, and polysaccharides such as alginate, heparin, and other naturally occurring biodegradable polymers of sugar units. Suitable examples of biodegradable polymers are shown in Table 1 and include, but are not limited to, polylactic acid, polyglycolic acid, polyhydroxybutyric acid, poly-γ-caprolactone, poly-δ-valerolactone, lactic acid-glycolic acid copolymer, poly(alpha-hydroxy acids), poly(lactones), poly(amino acids), poly(anhydrides), poly(orthoesters), poly(orthocarbonates) or poly(phosphoesters), or blends or copolymers of these polymers. Exemplary poly(alpha-hydroxy acids) include poly(glycolic acid), poly(DL-lactic acid), and poly(L-lactic acid). Exemplary poly(lactones) include poly(epsilon-caprolactone), poly(delta-valerolactone), poly(gamma-butyrolactone), poly(1,5-dioxepan-2-one), and poly(trimethylene carbonate).

The biodegradable polymer which can be desirably used in the present invention also includes poly-L-lactic acid (hereinafter referred to as "PLLA"), Poly-D,L-lactic acid (hereinafter referred to as "PDLLA"), and poly lactic-co-glycolic acid (hereinafter referred to as "PLGA"). Particularly, polylactic acid and lactic acid-glycolic acid copolymer (hereinafter referred to as "copoly(lactic/glycolic) acid"), having a molecular weight of 5,000 to 500,000 g/mole are more preferable. These polymers can be used either alone or in the form of a mixture of two or more thereof. Further examples of biodegradable polymers are set forth in Table 1 below.

TABLE 1

| Biodegradable polymer | | |
|---|---|---|
| Polymer | Classification | Specific polymer |
| Synthetic polymer | Polyesters | Poly(L-lactic acid), Poly(D,L-lactic acid), Poly(glycolic acid), Poly(lactic-co-glycolic acid), Polyhydroxybutyrate, poly(valerolactone), Poly(ε-caprolactone), |

TABLE 1-continued

Biodegradable polymer

| Polymer | Classification | Specific polymer |
| --- | --- | --- |
| | Polyanhydrides | Poly[bis(p-carboxyphenoxy)propane-cosebacic acid], Poly(fatty acid dimer-co-sebacic acid) |
| | Polyphosphazenes | Aryloxyphosphazene polymer |
| | Amino acid ester system | Poly(ortho esters) |
| Natural polymer | Polysaccharides | alginate, heparin, cellulose, starch, chondroitin sulfate polymer |
| | Proteins | Albumin, Collagen |

Biodegradable polymers have been the subject of numerous studies in controlled drug delivery (Conti et al., J. Microencapsulation 9: 153 (1992); Cohen and Bernstein, Microparticulate Systems for the Delivery of Proteins and Vaccines (Marcel Dekker Inc. 1996)). As drug carriers, microspheres formed from biodegradable polymer(s) have the advantages of providing a large surface area, being easily injected, and not requiring removal after completion of drug release. When used as an injectable drug delivery device, it has been found that drug release rate and microsphere interaction with cells are strongly dependent on the size distribution of the microspheres (Amsden and Goosen, J. Contr. Rel. 43: 183 (1997); Baker, Controlled Release of Biologically Active Agents (John Wiley 1987); Ishikawa. et al., J. Biomater. Sci., Polymer Ed. 2: 53 (1991)).

Accordingly, there are numerous publications disclosing studies directed towards developing methods to prepare polymeric microspheres under conditions that allow for controlling the average particle size, and particle size distribution, of the microspheres. These methods include dispersion polymerization of the monomer, potentiometric dispersion of dissolved polymer within an emulsifying solution followed by solvent evaporation, electrostatically controlled extrusion, injection of dissolved polymer into an emulsifying solution through a porous membrane followed by solvent evaporation and hot melt encapsulation (see, e.g., Kuriyama et al., J. Appl. Poly. Sci. 50: 107 (1993); Rembaum et al., U.S. Pat. No. 4,138,383; O'Donnell et al., J. Microencaps. 12: 155 (1995); Hommel et al., U.S. Pat. No. 4,956,128; Amsden and Goosen, J. Contr. Rel. 43: 183 (1997); Reyderman and Stavchansky, Pharm. Dev. Technol. 1: 223 (1996); Ipponmatsu et al., U.S. Pat. No. 5,376,347; Shiga et al., J. Pharm. Pharmacol. 48: 891 (1996), (Jameela et al., J. Biomater Sci Polym Ed 8: 457 (1997)).

Biodegradable microspheres can be prepared to include a drug or a therapeutic agent using any number of the methods, for example, as described by Mathiowitz and Langer, J. Controlled Release 5, 13-22 (1987); Mathiowitz, et al., Reactive Polymers 6, 275-283 (1987); and Mathiowitz, et al., J. Appl. Polymer Sci. 35, 755-774 (1988), the teachings of which are incorporated herein. The selection of the method depends on the polymer selection, the size, external morphology, and crystallinity that is desired, as described, for example, by Mathiowitz and Langer (J. Controlled Release 5: 13-22 (1987)); Mathiowitz et al. (Reactive Polymers 6: 275-283 (1987)); Mathiowitz et al. (J. Appl. Polymer Sci. 35: 755-774 (1988)); Mathiowitz, et al., Scanning Microscopy 4, 329-340 (1990); Mathiowitz, et al., J. Appl. Polymer Sci. 45, 125-134 (1992); and Benita, et al., J. Pharm. Sci. 73, 1721-1724 (1984), the teachings of which are incorporated herein. Methods include solvent evaporation, phase separation, spray drying, and hot melt encapsulation. U.S. Pat. Nos. 4,272,398, 3,773,919; 3,737,337; and 3,523,906 are representative of methods for making microspheres; hereby incorporated by reference.

Additional methods include vibratory excitation of a laminar jet of monomeric material flowing in a continuous liquid medium containing a suitable suspending agent, irradiation of slowly thawing frozen monomer drops, emulsification and evaporation, emulsification and evaporation using a high shear apparatus and a high hydrophobic phase to hydrophilic phase ratio, controlled polymerization in a solvent, non-solvent mixture, extrusion into a high shear air flow, and continuous injection of dissolved polymer into a flowing non-solvent through a needle oriented in parallel to the direction of flow of the non-solvent (see also, e.g., Timm and Coleman, U.S. Pat. No. 4,444,961; Rhim et al. U.S. Pat. No. 4,981,625; Sansdrap and Moes, Int. J. Pharm. 98: 157 (1993); Rourke, U.S. Pat. No. 5,643,506; Sosnowski et al., J. Bioact. Compat. Polym. 9: 345 (1994); Wang, U.S. Pat. No. 5,260,002; Leelarasamee et al., J. Microencaps. 5: 147 (1988)).

The microspheres are made of a biocompatible polymer and in a preferred embodiment are produced by a single emulsification process, similar to that described in U.S. Pat. No. 4,389,330 (Tice et al.). In the single emulsification process, a volatile organic solvent phase containing a biodegradable polymer, an aqueous solution necessarily containing an emulsifier such as polyvinyl alcohol, and a physiologically active substance are homogenized to produce an emulsion. The solvent is evaporated and the resulting hardened microspheres are freeze-dried. The microspheres of the preferred embodiment have an average size of 20 µm.

In one aspect of the drug delivery system of the invention, a drug or therapeutic agent is mixed with a biodegradable polymer to generate a microsphere according to methods known in the art. It is preferred to use a biodegradable polymer which dissolves in both water-immiscible organic solvents (e.g. methylene chloride, chloroform, carbon tetrachloride, dichloroethane, etc.) and water-miscible organic solvents (e.g. acetonitrile, acetone, etc.).

In a preferred embodiment, a biodegradable polymer is mixed with a suitable amount of a polymeric surfactant to prepare the microsphere of the invention. This polymeric surfactant is added in order to control the dissolution rate of microsphere and drug release rate. By altering the properties of the polymer and the properties of the dosage form, one can control the contribution of each of these release mechanisms and alter the release rate of the drug or therapeutic agent. Slowly eroding polymers such as poly L-lactide or high molecular weight poly(lactide-co-glycolide) with low glycolide compositions will cause the release to become diffusion controlled. Increasing the glycolide composition and decreasing the molecular weight enhances both water uptake and the hydrolysis of the polymer and adds an erosion component to the release kinetics. Any of polymeric surfactants may be preferably used without limitation provided that they are amphiphilic block copolymers having hydrophilic and hydrophobic groups, the example of which includes di-, tri- or multi-block copolymer or graft copolymer of the biodegradable polymer as mentioned in the above and polyethylene glycol. As such surfactant, polylactic acid-polyethylene glycol block copolymer is preferred, with poly-L-lactic acid-polyethyleneglycol di-block copolymer (PLLA-PEG, hereinafter, referred to as "DiPLE") or poly-L-lactic acid-polyethyleneglycol-poly-L-lactic acid tri-block copolymer (PLLA-PEG-PLLA, hereinafter, referred to as "TriPLE") being most preferred.

It should be noted that other methods of producing the microspheres may also be used under the present invention, such as a double emulsification process (Edwards et al., Science 276: 1868-1871, 1997), a phase inversion microencapsulation process (Mathiowitz et al., Nature 386: 410-413, 1997), or an atomization-freeze process (Putney and Burke, Nature Biotechnology 16: 153-157, 1998). It is well known to those skilled in the relevant art that the mixing ratio of the above biodegradable polymer and drug or therapeutic agent can be suitably determined according to the desired effects. In one aspect, the mixing ratio of drug or therapeutic agent and microsphere is within the range between 0.1 to about 70 wt % based on the weight of microsphere, and preferably within the range between 0.1 to about 50 wt % based on the weight of microsphere. It is desirable that the ratio be selected within the range of 10 to about 100 parts by weight based on the biodegradable polymer. The suitable particle sizes of the microspheres are within the range from 0.001 to about 1000 µm in diameter, preferably from 1 to 100 µm.

In another embodiment of the present invention, the drug delivery system comprises a microsphere comprising a drug or a therapeutic agent. A variety of techniques are known by which a drug or therapeutic agent can be incorporated into polymeric microspheres including, but not limited to, spary drying, solvent evaporation, phase separation, rapid freezing and solvent extraction. In spray drying, the polymer and factors are mixed together in a solvent for the polymer, then the solvent is evaporated by spraying the solution, leaving polymeric droplets containing the active agent. Spray drying is reviewed in detail by K. Masters in "Spray Drying Handbook" (John Wiley & Sons, New York 1984); and Patrick B. Deasy in "Microencapsulation and Related Drug Processes" (Marcel Dekker, Inc., New York 1984), the teachings of which are incorporated herein.

Solvent evaporation techniques can be used to form microspheres. These techniques involve dissolving the polymer in an organic solvent which contains either dissolved or dispersed active agent. The polymer/active agent solution is then added to an agitated continuous phase which is usually aqueous. Emulsifiers are included in the aqueous phase to stabilize the oil-in-water emulsion. The organic solvent is then evaporated over a period of several hours or more, thereby depositing the polymer around the core material. Solvent can be removed from the microspheres in a single step, as described in U.S. Pat. No. 3,737,337 and U.S. Pat. No. 3,523,906, or in U.S. Pat. No. 3,691,090 (under reduced pressure), or by the application of heat, as shown in U.S. Pat. No. 3,891,570. A two-step technique is described in U.S. Pat. No. 4,389,330. Freeze drying has also been used to remove the solvent from microspheres, as reported by Sato, et al, in "Porous Biodegradable Microspheres for Controlled Drug Delivery. I. Assessment of Processing Conditions and Solvent Removal Techniques," Pharmaceutical Research 5, 21-30 (1988). The teachings of these methods are incorporated herein.

Phase separation techniques can also be used to form microspheres. These techniques involve the formation of a water-in-oil emulsion or oil in water emulsion. The polymer is precipitated from the continuous phase onto the active agent by a change in temperature, pH, ionic strength or the addition of precipitants. For example, U.S. Pat. No. 4,675,800, et al., describes the formation of poly(lactic-co-glycolic) acid microspheres containing active proteins.

Polymer and agent to be encapsulated in solution are atomized using an ultrasonic device into a liquified gas. The atomized particles freeze when they contact the liquified gas (liquid nitrogen), forming frozen spheres. These sink to the surface of the frozen non-solvent (ethanol). The liquid gas is evaporated and the spheres begin to sink into the non-solvent as the non-solvent thaws. The solvent in the spheres is extracted into the non-solvent to form microspheres containing the agent to be encapsulated. Other non-solvents such as hexane are added to the non-solvent (ethanol) to increase the rate of solvent extraction from certain polymers, where appropriate, for example, when spheres are formed of polylactide-co-glycolide polymers.

Alternatively, a cold non-solvent for the polymer can be substituted for the combination of liquified gas-frozen non-solvent, provided the temperature of the non-solvent is below the freezing temperature of the polymer/active agent solution. It is important to select a solvent for the polymer having a higher melting point than the non-solvent for the polymer so that the non-solvent melts first, allowing the frozen microspheres to sink into the liquid where they later thaw. If a cold liquid non-solvent system for making the polymeric microspheres is used, the microspheres will sink immediately into the non-solvent. As the solvent in the microsphere thaws, it is extracted into the non-solvent. The solvent for the polymer and the non-solvent for the polymer must be miscible to allow extraction of the solvent from the microspheres.

In one aspect of the present invention, the prepared microsphere is mixed with the hydrogel after the hydrogel is prepared, and the resultant mixture is stirred at about room temperature for several hours in order to suspend the microspheres in the hydrogel. Any suitable method of mixing or contacting the microspheres with the hydrogel may be used.

The microspheres may contain at least one drug or therapeutic agent loaded into the microspheres or incorporated in the polymer forming the microspheres as described above. Alternately or in addition, a drug or therapeutic agent may also be included in the hydrogel, for example, incorporated in the polymer forming the hydrogel for short term effects or treatment. The drug or therapeutic agent is incorporated in the microsphere and/or hydrogel from about 0.1 to about 70% by weight, preferably from about 1 to about 50% by weight, and more preferably from about 1 to about 30% by weight. Although it should be noted that the drug or therapeutic agent can be incorporated to a weight percentage between 0.01 and 95 weight percentage of the microsphere and/or hydrogel. The amount or concentration of the drug or therapeutic agent included in the hydrogel and/or microsphere will depend on the absorption, inactivation, and excretion rates of the drug or therapeutic agent as well as the delivery rate of the polymers in the microsphere and/or the hydrogel. It is to be noted that dosage values will also vary with the type and severity of the disease, disorder, or condition being treated. It is to be further understood that for any particular subject, specific dosage regimens should be adjusted over time according to the individual need and the professional judgment of the person administering or supervising the administration of the compositions. In vivo dosages may be based on in vitro release studies in cell culture or on in vivo animal models.

Drugs or therapeutic agents that can be incorporated into the microspheres or hydrogel of the invention include therapeutic, diagnostic, and prophylactic agents. They can be naturally occurring compounds, synthetic organic compounds, or inorganic compounds. Substances that can be incorporated into the articles of the invention include proteins, polypeptides, carbohydrates, inorganic materials, antibiotics, antineoplastic agents, local anesthetics, antiangiogenic agents, vasoactive agents, anticoagulants, immunomodulators, cytotoxic agents, antiviral agents, antibodies, neurotransmitters, psychoactive drugs, oligonucleotides, lipids, cells, tissues, tissue or cell aggregates, and combinations thereof.

Other therapeutic agents include cancer chemotherapeutic agents, such as cytokines, chemokines, lymphokines, and substantially purified nucleic acids, and vaccines, such as attenuated influenza virus. Substantially purified nucleic acids that can be incorporated include genomic nucleic acid sequences, cDNAs encoding proteins, expression vectors, antisense molecules that bind to complementary nucleic acid sequences to inhibit transcription or translation, and ribozymes. For example, genes for the treatment of diseases such as cystic fibrosis can be administered. Polysaccharides, such as heparin, can also be administered.

Further examples of drugs capable of use according to the invention include local anesthetics such as: amethocaine, articaine, benzocaine, bupivacaine, chloroprocaine, dibucaine, dyclonine, etidocaine, levobupivacaine, lidocaine, mepivacaine, oxethazaine, pramoxine, prilocaine, procaine, proparacaine, and ropivacaine; narcotic analgesics such as: alfentanil, alphaprodine, buprenorphine, butorphanol, codeine, codeine phosphate, cyclazocine, dextomoramide, dezocine, diamorphine, dihydrocodeine, dipianone, fedotozine, fentanyl, hydrocodone, hydromorphone, ketobemidone, levorphanol, meptazinol, methadone, methadyl acetate, morphine, nalbuphine, norpropoxyphene, noscapine, oxycodone, oxymorphone, paregoric, pentazocine, pethidine, phenazocine, piritramide, propoxyphene, remifentanil, sufentanil, tilidine, and tramadol; and nonnarcotic analgesics such as: salicylates or phenylpropionic acid derivatives. Examples of appropriate solicylates include: aminosalicylic sodium, balsalazide, choline salicylate, mesalazine, olsalazine, para-amino salicylic acid, salicylic acid, salicylsalicylic acid, and sulphasalazine. Examples of appropriate phelypropionic acid derivatives include: ibuprofen, fenoprofen, flurbiprofen, ketoprofen, and naproxen.

The present invention describes a method for both short-term and long-term treatment of a disease, disorder or condition via controlled drug release. The composition of a temperature-sensitive hydrogel and a microparticle including at least one drug or therapeutic agent can be administered to a subject intravenously, intramuscularly, or subcutaneously or in other known ways appropriate to obtain the therapeutic effect desired. In a preferred embodiment, the composition is injected to a specific site (situs) in a subject. As it is in liquid phase while outside the subject's body, injection of the hydrogel-microsphere mixture is accomplished as easily as any other percutaneous injection. The conversion of the composition to a solid (gelatinous) phase shortly after injection is accomplished without the use of chemical cross-linkers. This solidification provides multiple benefits. For example, it keeps the drug or therapeutic agent localized at a particular site of interest, thereby maximizing the therapeutic effect of the injected drug or agent.

Figure 6:
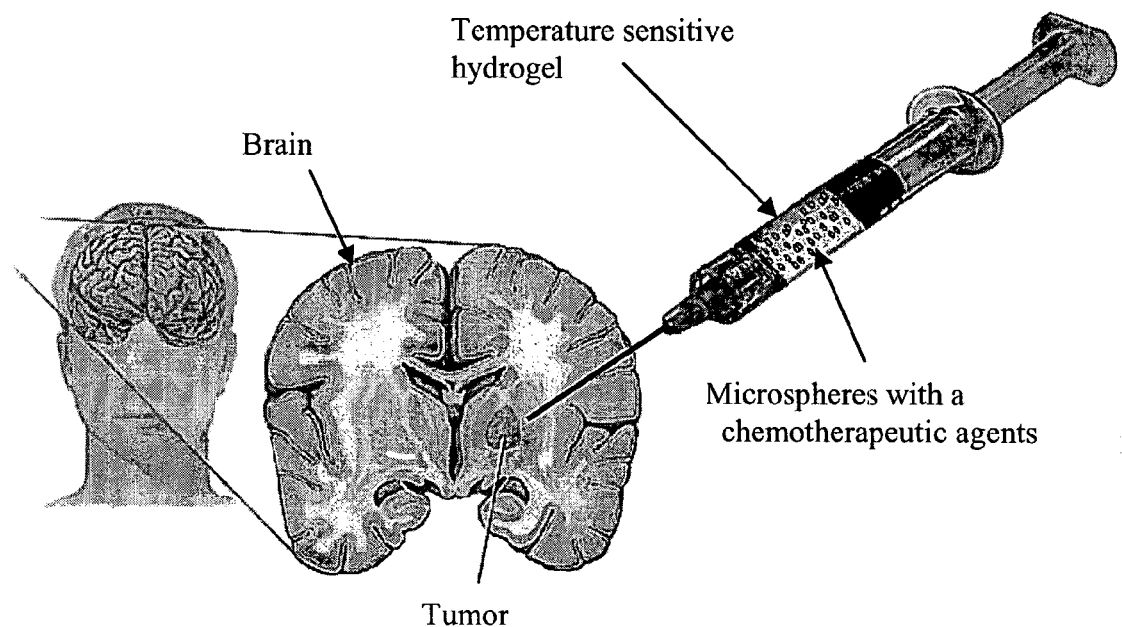
FIG. 6 shows a schematic of injection into the tumor site of liquid phase hydrogel through syringe.

After administration of the composition to a subject, in-situ gelation of the hydrogel containing microspheres occurs. The in-situ gelling system of one embodiment allows the controlled release of the drug or therapeutic agent in two diffusion steps: 1) diffusion of the drug or therapeutic agent molecules in the hydrogel into the affected tissues or cells for short-term effectiveness and 2) diffusion of microspheres containing a drug or therapeutic agent from the gel to the extracellular matrix of a subject for a long-term effect. The results of the treatment of a subject with a composition containing a drug or a therapeutic agent, as described herein, will vary according to the drug or a therapeutic agent being delivered. For example, if a composition containing an anesthetic was administered at the site of a painful joint, one would expect to observe pain relief in the joint of the subject as a result of the treatment. If a composition containing an anesthetic was administered into the epidural space in the back of a woman in labor, one would expect to observe pain relief in her lower body. If a chemotherapeutic agent is delivered through the delivery system to a tumor in a subject, one would expect to observe a decrease or regression in tumor growth or size in the subject as a result of the treatment. (See FIG. 6). Chemotherapeutic agents that may be used with the invention include, but are not limited to, alkylating agents, antimetabolites, antibiotics, natural or plant derived products, hormones and steroids (including synthetic analogs), and platinum drugs. One skilled in the art would be familiar with standard techniques and methods for determining tumor regression.

Figure 2:
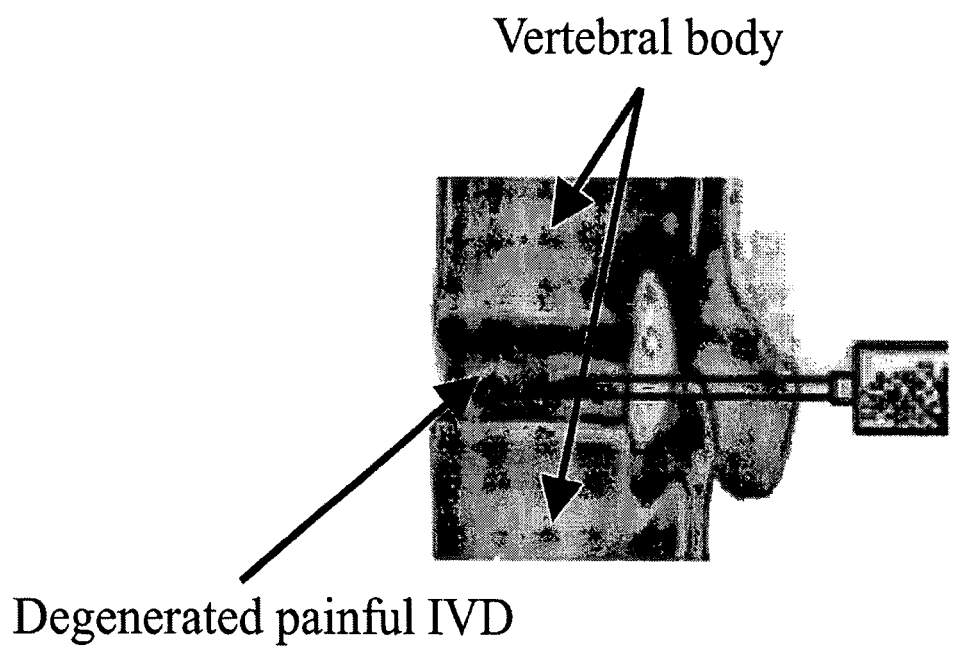
FIG. 2 shows the injection of the hydrogel and microspheres into a degenerated interverterbral disc according to the preferred embodiment.
Figure 3:
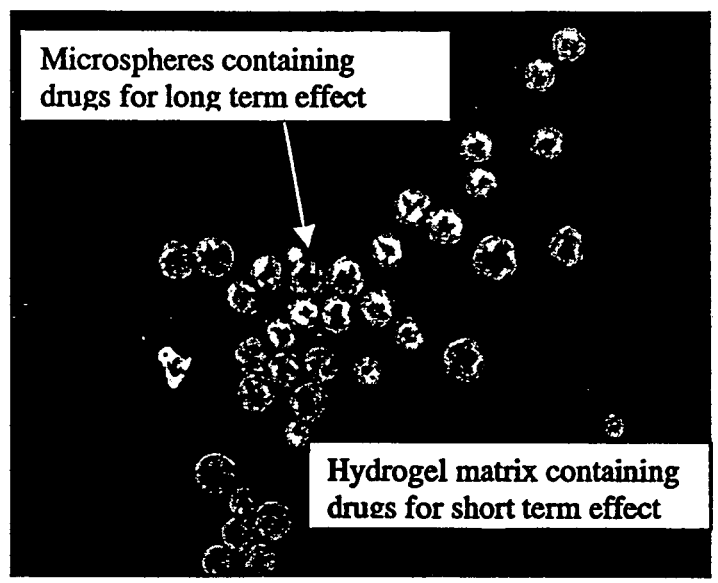
FIG. 3 illustrates the composition of the hydrogel-microsphere mixture according to the preferred embodiment of the invention.

In one embodiment, the composition is used to treat a degenerating interverterbral disc by injecting the aqueous composition including a local anesthetic into the degenerating disc in the subject, thereby providing pain relief. (See FIG. 2). Currently, local anesthetic agents are injected into the spinal area near but not into the nerve fibers. In terms of pharmacokinetics, the ester type local anesthetics undergo rapid hydrolysis by plasma cholinesterase and therefore typically have very short half-lives, e.g., less than one minute for procaine and chloroprocaine. The amide linkage also is hydrolyzed, but by liver microsomal enzymes, with the approximate order of the rates being etidocaine (fastest)>Lidocaine>mepivacaine>bupivacaine (slowest). As a result, toxicity from the amide local anesthetics is more likely to occur in patients with liver disease.

Depending on the dose or amount of the drug or therapeutic agent included in the composition and its location within the composition, e.g. the hydrogel or microspheres, the present invention describes methods and compositions for short-term or long-term treatment of a disease, disorder or condition via controlled release of a drug or a therapeutic agent. Thus, a composition of the present invention may be used to treat a subject in need thereof, for example, an animal, such as a mouse, rat, or human, by delivering the composition to the subject. As described, the composition may contain one or more drugs or therapeutic agents in the hydrogel or in the microsphere or in any combination thereof. Various routes of administration may be used to deliver the compositions of the present invention, as described above.

The methods and compositions of the present invention provide optimal delivery of a drug or therapeutic agent, because it releases the drug or therapeutic agent in a controlled manner. The result of controlled delivery is that the drug is delivered over a desired period of time. A slower and steadier rate of delivery may in turn result in a reduction in the frequency with which the drug or therapeutic agent must be administered to the animal.

The rate of release of a drug or therapeutic agent depends on many factors, for example, the composition of the polymers of the hydrogel and microspheres, and the degree of polymerization of the hydrogel. The rate of release of a drug or therapeutic agent also depends on the rate of degradation of the biodegradable polymer of the microsphere. For example, glycolic esters lead to very rapid degradation, lactic esters to somewhat slower degradation, and caprolactic esters to very slow degradation. When the degradable polymer consists of polyglycolic acid, the release period is less than one week. When the degradable polymer consists of poly(lactic acid), the release period is about one week. When the degradable polymer consists of a copolymer of caprolactone and lactic acid or a copolymer of trimethylene carbonate and lactic acid, the release period is two to four weeks. When the degradable polymer consists of poly(trimethylene carbonate) or a copolymer of caprolactone and trimethylene carbonate, the release period is about three to eight weeks. When the degradable polymer consists of poly(trimethylene carbonate) or poly(caprolactone), the release period is longer than about five weeks. The rate of release of a given drug or therapeutic agent from a microsphere or hydrogel also depends on the quantity of the loaded drug or therapeutic agent as a percent of the final product formulation.

Yet another factor that affects the release rate of a drug or therapeutic agent from a microsphere is the particle size of the drug or therapeutic agent. By adjusting the factors discussed above, degradation, diffusion, and controlled release may be varied over very wide ranges. For example, release may be designed to occur over hours, days, or months.

Although various aspects of the composition are described in detail, it will be apparent to one skilled in the art that modifications, substitutions, and additions may be made without departing from the spirit and scope of the invention. All patents, patent applications, articles and publications mentioned herein, both supra and infra, are hereby incorporated herein by reference.

EXAMPLES

Example 1

Preparation of Microspheres

Microsphere by Solvent Evaporation.

Five % (w/v) of PCL (Mw: 65000 Da) and 1% (w/v) of drug were dissolved in methylene chloride (MC). Resultant solution was homogenized at about 3000 rpm for 2 min at room temperature. It was then poured and agitated at 500 rpm in 100 ml of 1% (w/v) polyvinyl alcohol (PVA) for 4 hrs at room temperature. After being hardened, the MSs will be collected by centrifugation (10 min at 4000 rpm), washed three times with 10 ml of ultra pure water, and lyophilized by a freezer. The mean diameter of the lyophilized MSs will be 20 μm within a standard deviation of ±10 μm.

Microspheres by Hot Melt Encapsulation:

Five % (w/v) of PCL powders was melted in 10 ml of deionized water at 70 deg C., and the mixture was agitated thoroughly by vortex for 1 minute. It was then suspended in 200 ml of water solvent that was heated 5 deg C. above the melting point of the PCL and stirred with a four-blade impeller continuously at 1000 rpm for 2 hours. The water solvent contained 1% (w/v) of Poly(EO-PO-EO) with respect, to external phase. Once the emulsion was stabilized, it was cooled till the core material solidified. (Jameela et al. J Biomater Sci Polym Ed 8(6): 457 (1997), Lin and Yu J Microencapsul 18(5): 585 (2001), Lin and Kang. J Microencapsul 20(2): 169 (2003), Cortesi et al. Biomaterials 23(11): 2283 (2002), Reithmeier et al. J Control Release 73(2-3): 339 (2001)).

Formulation of a Drug Carrier:

POLOXAMER® polymers (15 to 25% (w/v)) and sodium hyaluronate (0.2% (w/v) to 1.5% (w/v)) were dissolved in deionzed water. It was then stirred at 100 rpm for another 4 hours at room temperature after adding microspheres to the resultant solution. It was finally stored in a refrigerator until percutaneous injection into the affected area of the intervertebral disc. Immediately prior to the injection, the microspheres containing a therapeutic agent will be mixed with the stored hydrogel in solution phase.

Example 2

Intradiscal Drug Delivery System for the Treatment of Discogenic Low Back Pain

Introduction:

Low back pain (LBP) ranks $2^{nd}$ among common medical symptoms, $5^{th}$ in causes of hospitalization, and $3^{rd}$ in leading to surgical procedures in the USA. Degenerative disc disease (DDD) is generally considered as a major cause of LBP. Immunohistochemical studies showed LBP as microvascular blood vessels accompanied nerve fibers growing into the pain level disc and these are expressed as nerve growth factor[1]. LBP treatments include medication, steroid injection, physical therapy, surgery, etc. Most are temporal pain relief or destructive to the disc requiring post-surgical care with high complication rates, and often lead to instability of the motion segments. One of the solutions to the LBP would be an injectable carrier that provides a long-term pain relief without destroying the disc. The objective of this study is to develop a microsphere (MS)-dispersed in-situ forming hydrogel matrix, which contains pain relieving drug(s) in both the MS and the matrix.

Materials and Methods:

Microsphere (MS) Preparation by Melt Encapsulation:

Poly(ε-caprolactone) (PCL) (5% (w/v)) in deionized water was melted at 70° C. Bupivacaine free base (BB) drug was mixed into the solution. It was then transferred to the water containing 1% (w/v) of poly(ethylene oxide-propylene oxide-ethylene oxide) (poly(EO-PO-EO)) at 65° C. for 2 hrs. The solution was cooled down and dried till MS hardened.

Development of In-Situ Forming Gel:

Bupiv was suspended in deionized water. MS loaded with Bupiv BB was added. To form a chemically cross-linked gel, fifteen to 35% (w/v) of poly(EO-PO-EO), 0 to 1.0% (w/v) of sodium hyaluronate (SH) and 2% (w/v) 1-ethyl-3-(3-dimethyl aminopropyl) carbodiimide hydrochloride (CDI) were dissolved in the above solution. Physically cross-linked gels were formed by omitting CDI. For solutions with CDI, pH was adjusted to 5.5 by adding 0.1 N of HCl.

Determination of Relation Temperature:

Viscosity of gel at a shear rate of 1 $sec^{-1}$ was measured using a viscometer (HB DV-II, Brookfield Engineering Lab., Middleboro, Ma.) equipped with a 1.0 mm gap cone and plate (CP 52). Viscosity versus temperature curves at equilibrium showed three regions, i.e., sol, transition, and gel phases. The gelation temperature was determined using the midpoint of the transition phase.

Measurement of volume change: A 2.0 ml sample was immersed into a glass tube (i.d. 0.5 mm) in a temperature controlled incubator (417, Lab-line Instruments Inc., Melrose, Ill.). At each equilibrium temperature from 20° C. to 40° C., volume change was monitored by a video camera and quantified by image software (Image J, NIH).

In-Vitro Drug Release Test:

A basket containing the gel was rotated at 50 rpm in 900 ml of PBS at pH 7.4 and 37° C. in a dissolution apparatus (D-800 Dissolution Tester, Logan, Utah). At regular time intervals, 1 ml PBS solution was collected and the same amount of a fresh PBS solution was added. The amount of Bupiv released from the gel was analyzed at 274 nm using HPLC (Alliance HT LC/MS, Waters, Milford, Ma.).

Figure 4:
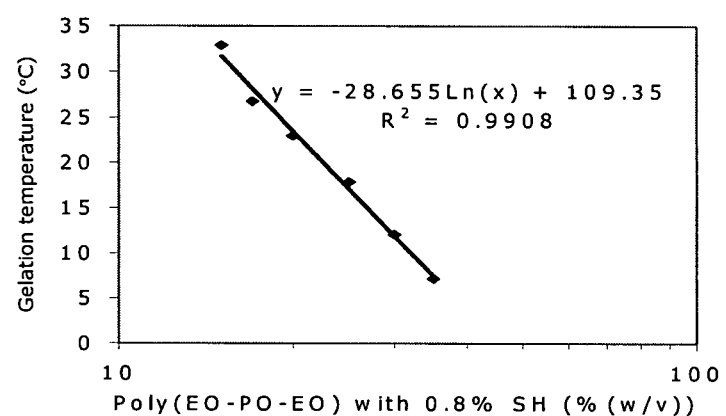
FIG. 4 shows gelation temperature vs. amount of poly(EO-PO-EO) with 0.8% SH.

Results:

MS showed spherical shape with smooth surface and an average diameter of 22.2±4.0 μm. Viscosity of the gels were 220, 326, and 426 Pa·s for 0, 0.4, and 0.8% SH, respectively. Gelation temperature decreased with increasing poly(EO- PO-EO) concentration as shown in FIG. 4. Volume change was proportional to the temperature. Volumes of the gels with 15, 17, and 20% of poly(EO-PO-EO) plus 0.8% of SH showed increases of 1.5, 1.3, and 1.1%, respectively.

Discussion:

Comparing 5% PCL based melt encapsulation with 10% PCL based oil-in-water solvent evaporation, the characteristics of MS showed similar size (≈25 μm) and higher yields (≈90%), but the former can be better since it does not use an organic solvent. The in-situ forming gels range from soft to firm depending on the ratio of poly(EO-PO-EO) and SH. The effect of concentration and temperature on viscosity suggests that poly(EO-PO-EO) induces the sol to gel transition at higher temperature by physical entanglements. In addition, CDI as a cross-linker reacted with SH to increase gel strength, which was confirmed by the increase in viscosity. The SH contributes structural integrity of the gel by increasing the degree of cross-linking. The volume change possibly is explained by the cluster formation of hydrophobic chains in the gel state. Energy minimization leads to formation of more compact hydrophobic chains accompanied by the exclusion of water, leading to a slight volume increase.

REFERENCE

1. Freemont, A. J., et al., J Pathol, 2002. 197(3): p. 286-92.

Example 3

Development of Nucleoplasty by In-Situ Forming Hydrogels

Introduction

Nucleoplasty, the replacement of the nucleus pulposus (NP), is a viable option for surgical treatment of degenerative disc along with total disc replacement and intervertebral body fusion. In-situ forming nucleus prosthesis having mechanical, chemical, surface, and viscoelastic compatibility are being investigated. The objective of this study was to develop the in-situ forming nucleoplasty that addresses some of these issues.

Materials and Methods

Preparation of the In-Situ Forming Hydrogel:

The in-situ forming gels were first prepared by dissolving 15 to 20% (w/v) of poly(ethylene oxide-propylene oxide-ethylene oxide) (poly(EO-PO-EO)) and 0.2 to 1.0% (w/v) sodium hyaluronate (SH) in deionized water at an ambient temperature. Two % (w/v) of 1-ethyl-3-(3-dimethylaminopropyl)carbodiimide hydrochloride (CDI) as a cross-linker was added to the solution[1]. The pH was adjusted to 5.5 by 0.1N HCl. After stirring for 1 min, the solution was left on the shaker for 24 hrs to produce a gel. It was then stirred at 100 rpm for another 4 hours at room temperature after adding microspheres to the resultant solution.

Viscoelastic Test:

The dynamic viscoelastic parameters were determined in oscillatory mode using a Haake RS-1 equipped with a cone and plate system (C35/4, 35 mm diameter, 4° angle) and a temperature control system (Haake F3-CH circulator). The measurement gap was 0.140 mm and about 0.8 ml was loaded on the sample plate. A strain amplitude sweep test was conducted at 1 Hz using non-destructive dynamic Theological testing in order to measure the complex modulus ($G^*$) as a function of strain. The linear viscoelastic region of the sample was determined from the $G^*$-strain curves. A strain value from the linear viscoelastic region was set to 0.3% during the frequency sweep tests, and the frequency was ramped from 0.1 to 20 Hz. Changes in viscoelastic parameters over frequency range were obtained.

Results

Viscosity was increased with increasing poly(EO-PO-EO) concentration at a constant SH concentration. The similar trend was observed for the controls, poly(EO-PO-EO) or SH itself, with lower viscosity. The increase in viscosity was also influenced by temperature increase. In a comparison of the physical- and chemical cross-linked hydrogels based on 20% poly(EO-PO-EO) and 0.8% SH at 37° C., the latter showed as high as 40% higher viscosity, which corroborates chemical cross-linking reaction.

Figure 5:
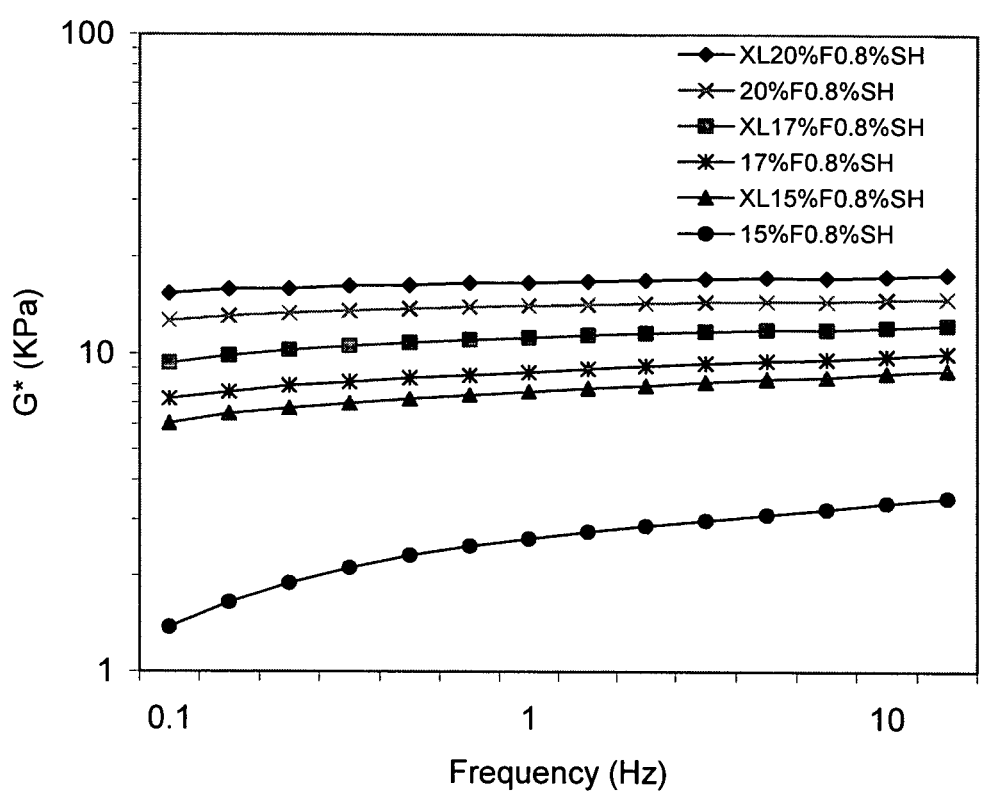
FIG. 5 shows gel concentration on the complex modulus (G*). XL: CDI cross-linked. The G* increased with increasing poly(EO-PO-EO) concentration. In particular, the in-situ gel formed by 15% poly(EO-PO-EO) plus 0.8% SH showed the most frequency dependence while the rest of gels became lesser one depending on poly(EO-PO-EO) concentration. Chemically cross-linked gels by CDI showed higher G*, indicating a stiffer gel. Higher poly(EO-PO-EO) concentration would bring more polymer-polymer interactions, resulting in more rigid network structure. *Detailed experimental protocols are described in Example 3.

Frequency ramp profiles with or without CDI at 37° C. are shown in FIG. 5. The $G^*$ increased with increasing poly(EO-PO-EO) concentration. Fifteen % concentration showed the most frequency dependence while the rest of samples became lesser frequency dependence due to the increasing poly(EO-PO-EO) concentration. Over the frequency range from 0.1 to 20 Hz, $G^*$ of the hydrogel with CDI varied from 7 to 18 KPa and a phase angle (δ) from 4 to 13°, the hydrogel without CDI were 1 to 15 KPa and 4 to 23°.

Discussion

The in-situ formed hydrogels showed low viscosity at room (low) temperature and higher viscosity at higher temperature (37° C.) becoming a gel. This low viscosity with liquid like behavior could help the injectability of a gel into the target space with minimal opening. Chemically cross-linked gels by CDI showed higher $G^*$, indicating a stiffer gel. Generally, higher poly(EO-PO-EO) concentration would bring more polymer-polymer interactions, resulting in more rigid network structure. Our in-situ gelling system exhibited excellent viscoelastic properties over 1-100 Hz range, comparable to those of the normal NP of the human disc ($G^*$=7-21 KPa and δ=23-31°)[2]. These suggest that temperature sensitive in-situ forming hydrogel may be a promising material for nucleoplasty for further investigations.

REFERENCES

1. Taguchi, T. and J. Tanaka, J Biomater Sci Polym Ed, 2002. 13(1): p. 43-52.
2. Iatridis, J. C., et al., Spine, 1996. 21(10): p. 1174-84.

Example 4

Drug Delivery System for the Treatment of Tumors

Microsphere (MS):

Poly(ε-caprolactone) (PCL) (5% (w/v)) in deionized water was melted at 70° C. Hydrophobic anticancer drug was mixed into the solution. It was then transferred to the water containing 1% (w/v) of poly(ethylene oxide-propylene oxide-ethylene oxide) (P127) at 65° C. for 2 hrs. The solution was cooled down and dried till MS hardened.

In-Situ Forming Gel:

Hydrophobic anticancer drug was suspended in deionized water as well. MS containing a drug was added. To form a chemically cross-linked gel, fifteen to 35% (w/v) of P127, 0 to 1.0% (w/v) of sodium hyaluronate (SH) and 2% (w/v) 1-ethyl-3-(3-dimethyl aminopropyl)carbodiimide hydrochloride (EDC) were dissolved in the above solution. Physically cross-linked gels were formed by omitting EDC. For solutions with EDC, pH was adjusted to 5.5 by adding 0.1 N of HCl.

Determination of Gelation Temperature:

Viscosity of gel at a shear rate of 1 sec$^{-1}$ was measured using a viscometer (HB DV-II, Brookfield Engineering Lab., Middleboro, Ma.) equipped with a 1.0 mm gap cone and plate (CP 52). Viscosity versus temperature curves at equilibrium showed three regions, i.e., sol, transition, and gel phases. The gelation temperature was determined using the midpoint of the transition phase.

Measurement of Volume Change:

A 2.0 ml sample was immersed into a glass tube (i.d. 0.5 mm) in a temperature controlled incubator (417, Lab-line Instruments Inc., Melrose, Ill.). At each equilibrium temperature from 20° C. to 40° C., volume change was monitored by a video camera and quantified by image software (Image J, NIH).

Viscoelastic Test:

The dynamic viscoelastic parameters were determined in oscillatory mode using a Haake RS-1 equipped with a cone and plate system (C35/4, 35 mm diameter, 4° angle) and a temperature control system (Haake F3-CH circulator). The measurement gap was 0.140 mm and about 0.8 ml was loaded on the sample plate. A strain amplitude sweep test was conducted at 1 Hz using non-destructive dynamic rheological testing in order to measure the complex modulus (G*) as a function of strain. The linear viscoelastic region of the sample was determined from the G*-strain curves. A strain value from the linear viscoelastic region was set to 0.3% during the frequency sweep tests, and the frequency was ramped from 0.1 to 20 Hz. Changes in viscoelastic parameters over frequency range were obtained.

REFERENCES CITED

1. Langer et al.: U.S. Pat. No. 5,626,862 A May 1997
2. Sawhney: U.S. Pat. No. 6,632,457 B1 October 2003
3. Christopher, G., et al., *Recent advances in brain tumor therapy: local intracerebral drug delivery by polymers*. Investigational New Drugs, 2004.22: p. 27-37.
4. Moore, T., et al., *Experimental investigation and mathematical modeling of Pluronic F127 gel dissolution: drug release in stirred systems*. J Control Release, 2000. 67(2-3): p. 191-202.

Example 5

Figure 7:
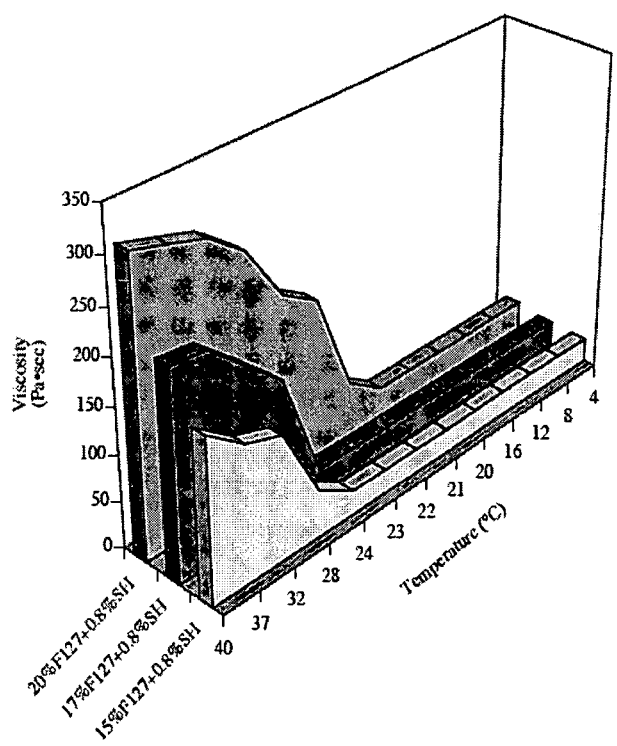
FIG. 7 illustrates viscosity versus temperature for 15, 17 and 20% copolymer plus 0.8% SH solution (n=3).
Figure 8:
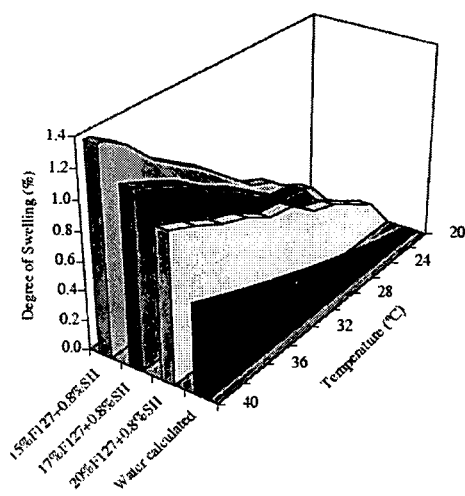
FIG. 8 illustrates percent swelling versus temperature for 15, 17 and 20% copolymer plus 0.8% SH solution (n=3).
Figure 9:
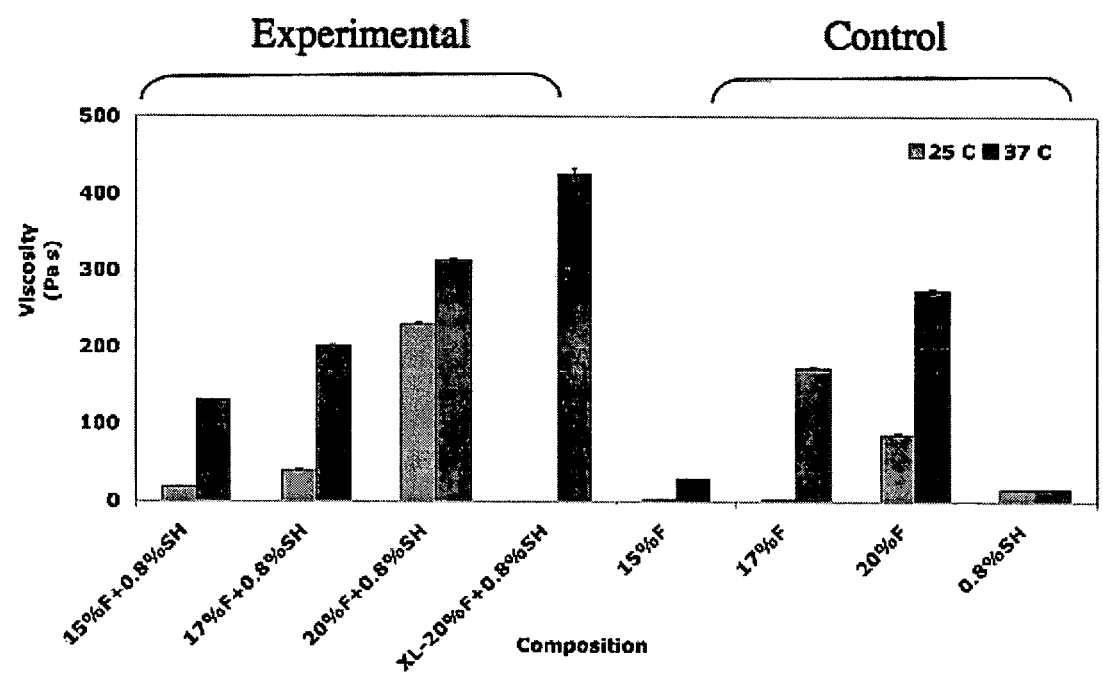
FIG. 9 illustrates temperature effect on viscosity ($\eta$) of hydrogel matrix (n=3). Viscosity was not only increased with increasing poly(EO-PO-EO) concentration, but increased with temperature at a constant SH concentration. In a comparison of the physical- and chemical cross-linked hydrogels, the latter showed as high as 40% higher viscosity. The in-situ forming gels showed low viscosity at lower temperature and then shifted to higher viscosity with increasing temperature, becoming a semi-solid like gel.
Figure 10:
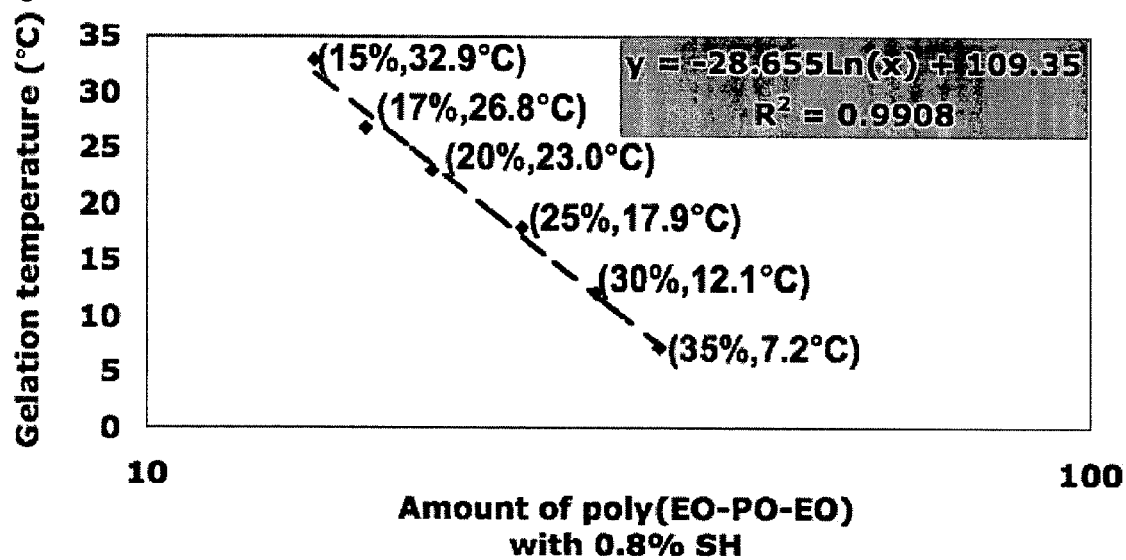
FIG. 10 illustrates effect of poly (EO-PO-EO) on gelation temperature (n=3). Gelation temperature was inversely proportional to the poly(EO-PO-EO) concentration with an excellent linearity.
Figure 11:
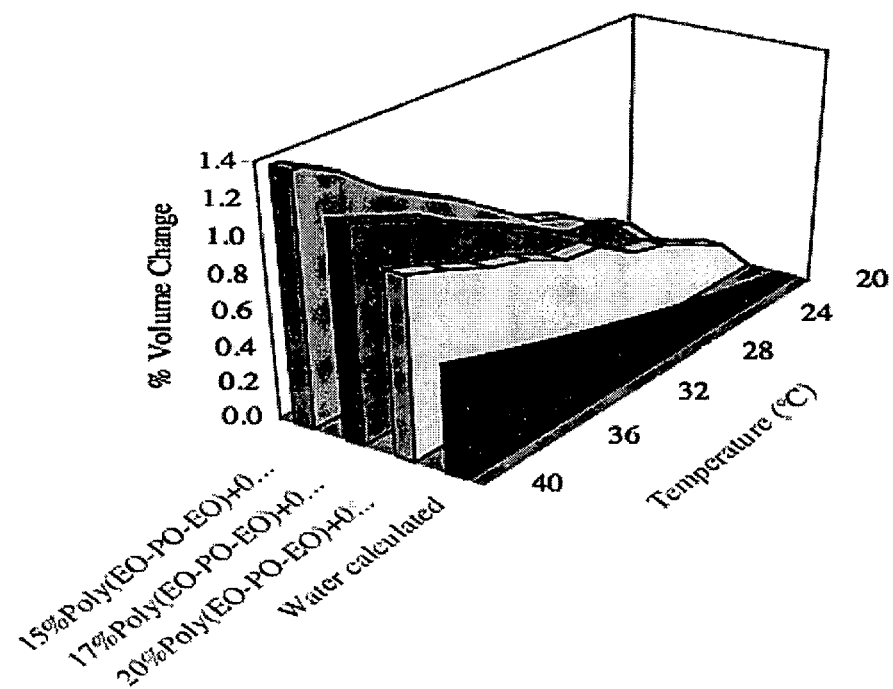
FIG. 11 illustrates thermal volume change. Overall volume change of the physically entangled gel continuously showed a temperature dependency, probably because of the more increasing local micellization of poly(EO-PO-EO) over 20-40 temperature range. The in-situ formed gel by 15% of poly(EO-PO-EO) plus 0.8% SH showed the largest volume change. With increasing temperature, the in-situ forming gel tended to minimize its energy by folding; the propylene oxide block exposed to water and coiling them together into a small hydrophobic block with less surface area exposed to the aqueous environment. A more compact hydrophobic block might make an exclusion of water by a much more favorable arrangement.
Figure 12:
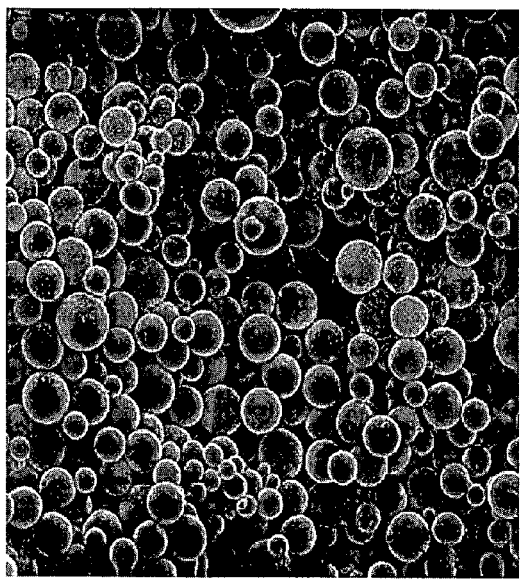
FIG. 12 illustrates MS morphology formed by melt encapsulation. Examination of the surface morphology of the particles at higher magnification revealed a fairly smooth non-porous surface. The average diameter and size distribution were computed by the particle size analyzer called Image J (free download from NIH). Average diameter and standard deviation of MS were determined to $4.77 \pm 1.49$ μm
Figure 12:
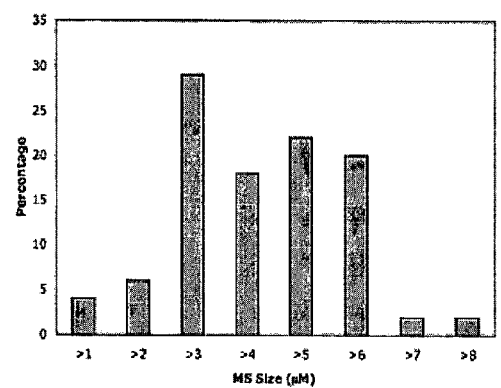
Figure 13:
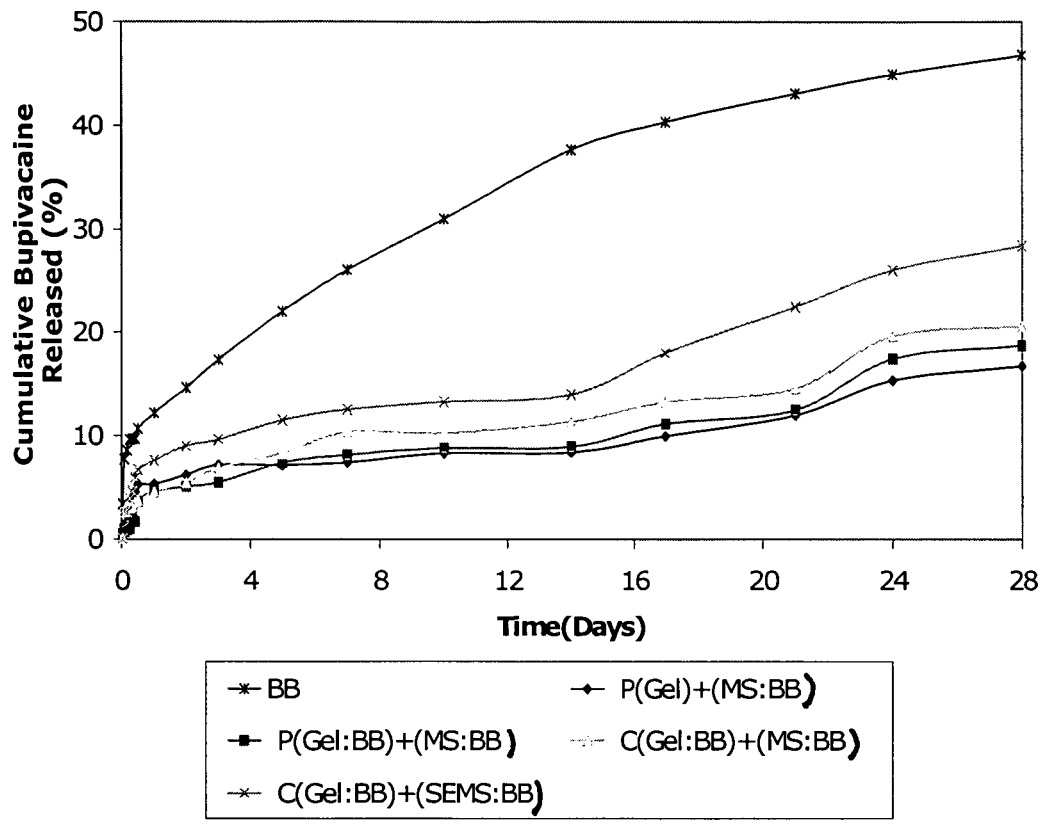
FIG. 13 illustrates in vitro release of bupivacaine. The release rate from melt encapsulated MS containing BB was slower than that from solvent evaporated MS during 28 days. The BB entrapped in the matrix was more tightly bound and the mechanism of release followed diffusion process since Poly($\epsilon$-caprolactone) (PCL) degraded very slowly. Once the diffusion started, the channels provided a pathway for continuous diffusion of the BB.
Figure 14:
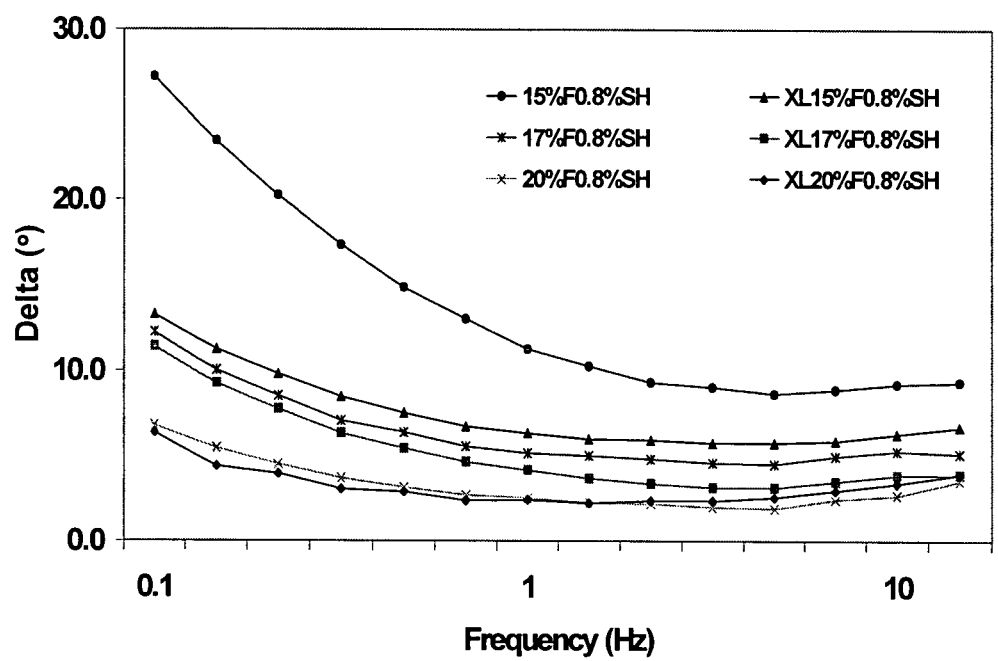
FIG. 14 shows phase angle behavior of the in-situ forming gel in the dynamic frequency sweep experiment. Over the frequency range of 0.1-20 Hz, G* of the gel with CDI varied from 7-18 KPa and a phase angle (d) from 4-13°, the gel without CDI were 1-15 KPa and 4-23°. *Detailed experimental protocols are described in Example 3.

MS showed spherical shape with smooth surface and an average diameter of 4.77±1.49 μm. Comparing 5% PCL based melt encapsulation with 10% Poly(ϵ-caprolactone) (PCL) based oil-in-water solvent evaporation, MS showed similar size (≈5 μm) and higher yields (≈90%), but the former can be better since it does not use an organic solvent. Viscosity, representing gel strength in the fluid motion near a solid boundary, strongly depended on F127 polymers, also known by the generic name Poly(EO-PO-EO), concentration and temperature (for example, 426 Pa·s for 0.4% Poly(EO-PO-EO) plus 0.8% SH at 37° C.) as shown in FIG. 7. Gelation temperature decreased with increasing Poly(EO-PO-EO) concentration. The effect of concentration and temperature on viscosity suggests that Poly(EO-PO-EO) induces the sol to gel transition at higher temperature by physical entanglements. Similar observations were seen in other Pluronic gel formulations(2). An explanation of this behavior is a result of micellar entanglements and packing. As a result of this more rigid gel, micelles are difficult in separating easily from each other, which accounts for lower volume change and sustained drug release. By altering the parameters of gel preparation, the rate of gelation upon 2 ml in a vial was shown to be 1.5 to 2 min. Volume change was proportional to the temperature. Volumes of the gels with 15, 17, and 20% of Poly(EO-PO-EO) plus 0.8% of SH showed increases of 1.5, 1.3, and 1.1%, respectively (FIG. 8). The discrepancy in the volume change is possibly explained by the extent of cluster formation of hydrophobic chains in the gel state. Energy minimization leads to formation of more compact hydrophobic chains with increasing Poly(EO-PO-EO) accompanied by the exclusion of water, leading to a slight volume increase.

REFERENCES CITED

1. Langer et al.: U.S. Pat. No. 5,626,862 A May 1997
2. Sawhney: U.S. Pat. No. 6,632,457 B1 October 2003
3. Christopher, G., et al., *Recent advances in brain tumor therapy: local intracerebral drug delivery by polymers*. Investigational New Drugs, 2004. 22: p. 27-37.
4. Moore, T., et al., *Experimental investigation and mathematical modeling of Pluronic F127 gel dissolution: drug release in stirred systems*. J Control Release, 2000. 67(2-3): p. 191-202.

REFERENCES

1. Jameela S R, Suma N, Jayakrishnan A. Protein release from poly(epsilon-caprolactone) microspheres prepared by melt encapsulation and solvent evaporation techniques: a comparative study. J Biomater Sci Polym Ed 1997; 8(6): 457-66.
2. Lin W J, Yu C C. Comparison of protein loaded poly (epsilon-caprolactone) microparticles prepared by the hot-melt technique. J Microencapsul 2001; 18(5): 585-92.
3. Lin W J, Kang W W. Comparison of chitosan and gelatin coated microparticles: prepared by hot-melt method. J Microencapsul 2003; 20(2): 169-77.
4. Cortesi R, Esposjto E, Luca G, Nastruzzi C. Production of lipospheres as carriers for bioactive compounds. Biomaterials 2002; 23(11): 2283-94.
5. Reithmeier H, Herrmann J, Gopferich A. Lipid microparticles as a parenteral controlled release device for peptides. J Control Release 2001; 73(2-3): 339-50.
6. Freemont, A. J., et al., J Pathol, 2002. 197(3): p. 286-92.
7. Taguchi, T. and J. Tanaka, J Biomater Sci Polym Ed, 2002. 13(1): p. 43-52.
8. Iatridis, J. C., et al., Spine, 1996. 21(10): p. 1174-84.
9. Langer et al.: U.S. Pat. No. 5,626,862 A May 1997
10. Sawhney: U.S. Pat. No. 6,632,457 B1 October 2003
11. Christopher, G., et al., *Recent advances in brain tumor therapy: local intracerebral drug delivery by polymers*. Investigational New Drugs, 2004. 22: p. 27-37.
12. Moore, T., et al., *Experimental investigation and mathematical modeling of Pluronic F127 gel dissolution: drug release in stirred systems*. J Control Release, 2000. 67(2-3): p. 191-202.

What is claimed is:

1. A method of introducing a drug or therapeutic agent to a specific site within an animal comprising:
   introducing to a specific site in an animal a microsphere-hydrogel mixture comprising: a plurality polymer microspheres comprising a drug or therapeutic agent, said microspheres suspended in a dispersion within a temperature sensitive hydrogel, wherein said hydrogel is comprised of at least 15% but no more than 20% synthetic polymer and at least 0.2% but no more than 1% hyaluronic acid and the hydrogel is in liquid state at or about room temperature and a solid or gelatinous state at or about body temperature, wherein said microspheres comprise between about 10% and about 50% of the microsphere-hydrogel mixture, wherein said drug or therapeutic agent is from about 0.1% to about 70% of said microsphere, hydrogel or microsphere-hydrogel mixture and wherein the drug or therapeutic agent is released at said site.

2. The method of claim 1 wherein said step of introducing is by injection.

3. The method of claim 1 wherein the hydrogel comprises at least one drug or therapeutic agent to provide a short-term therapeutic effect.

4. The method of claim 1 wherein the microsphere, hydrogel, or microsphere-hydrogel mixture comprises a drug or therapeutic agent from about 0.1% to about 70% of the microsphere, hydrogel, or microsphere-hydrogel mixture.

5. The method of claim 1, wherein the synthetic polymer is selected from the group consisting of: N-isopropyl acrylamide polymer, ethylhydroxyethylcellulose, poly(etheylene oxide-b-propylene oxide-b-ethylene oxide), poloxamers, PLURONICS® polymers, poly(ethylene glycol)/poly(D,L-lactic acid-co-glycolic acid) block co-polymers, polysaccharides, alginate, polyphosphazines, polyacrylates, TETRONICS™ polymers, polyethylene oxide-polypropylene glycol block copolymers and derivatives and analogs thereof.

6. The method of claim 1 wherein the microspheres comprise between about 10% to about 50% of the microsphere-hydrogel mixture.

7. The method of claim 1 wherein the drug or therapeutic agent is released from the microspheres in a controlled manner for a long-term therapeutic effect.

8. The method of claim 1 wherein said microspheres comprise biodegradable polymers selected from the group consisting of:

polylactic acid, polyglycolic acid, polyhydroxybutyric acid, poly-γ-caprolactone, poly-δ-valerolactone, lactic acid-glycolic acid copolymer, poly(alpha-hydroxy acids), poly(lactones), poly(amino acids), poly(anhydrides), poly(orthoesters), poly(orthocarbonates) or poly(phosphoesters), poly(DL-lactic acid), poly(L-lactic acid), poly(lactones), poly(epsilon-caprolactone), poly(delta-valerolactone), poly(gamma-butyrolactone), poly(1,5-dioxepan-2-one), and poly(trimethylene carbonate), poly lactic-co-glycolic acid, poly(valerolactone), poly(ε-caprolactone) (PCL), Poly[bis(p-carboxyphenoxy)propane-cosebacic acid], poly(fatty acid dimer-co-sebacic acid), aryloxyphosphazene polymer, blends and copolymers of these polymers.

9. The method of claim 1 wherein the drug or therapeutic agent is a local anesthetic selected from the group consisting of: amethocaine, articaine, benzocaine, bupivacaine, chloroprocaine, dibucaine, dyclonine, etidocaine, levobupivacaine, lidocaine, mepivacaine, oxethazaine, pramoxine, prilocalne, procaine, proparacaine, and ropivacaine.

10. The method of claim 1 wherein the drug or therapeutic agent is a narcotic analgesic selected from the group consisting of: alfentanil, alphaprodine, buprenorphine, butorphanol, codeine, codeine phosphate, cyclazocine, dextomoramide, dezocine, diamorphine, dihydrocodeine, dipianone, fedotozine, fentanyl, hydrocodone, hydromorphone, ketobemidone, levorphanol, meptazinol, methadone, methadyl acetate, morphine, nalbuphine, norpropoxyphene, noscapine, oxycodone, oxymorphone, paregoric, pentazocine, pethidine, phenazocine, piritramide, propoxyphene, remifentanil, sufentanil, tilidine, and tramadol.

11. The method of claim 1 wherein the drug or therapeutic agent is a nonnarcotic analgesic selected from the group consisting of: aminosalicylic sodium, balsalazide, choline salicylate, mesalazine, olsalazine, para-amino salicylic acid, salicylic acid, salicylsalicylic acid, and sulphasalazine, ibuprofen, fenoprofen, flurbiprofen, ketoprofen, and naproxen.

12. The method of claim 1, wherein the mixture is delivered to a site of musculoskeletal joint pain in an animal, wherein said drug is released at said site thereby providing pain relief.

13. The method of claim 12 wherein at least one site of musculoskeletal joint pain comprises an interverterbral disc, a hip, a knee, or an ankle.

14. The method of claim 1 wherein a chemotherapeutic drug or agent is delivered to a site of a tumor in an animal, wherein said drug or agent is released at said site thereby causing tumor regression.

15. The method of claim 14, wherein said chemotherapeutic drug or agent is selected from the group consisting of: alkylating agents, antimetabolites, antibiotics, natural or plant derived products, hormones and steroids and platinum drugs.

16. A method of treating back pain through controlled drug release comprising:

injecting a pharmaceutical composition percutaneously into at least one interverterbral discs, said pharmaceutical composition comprising:

a temperature-sensitive hydrogel, wherein the hydrogel is comprised of at least 15% but no more than 20% synthetic polymer and at least 0.2% but no more than 1% hyaluronic acid and the hydrogel is in liquid state at or about room temperature and a solid or gelatinous state at or about body temperature; and non-porous microspheres of biodegradable polymers comprising at least one pain relieving drug suspended in a dispersion within said temperature-sensitive hydrogel, wherein the microspheres comprise between about 10% and about 50% of the microsphere-hydrogel mixture, and wherein said drug or therapeutic agent is from about 0.1% to about 70% of said microsphere, hydrogel or microsphere-hydrogel mixture; and releasing said pain relieving drug by diffusion from or degradation of said hydrogel.

17. The method of claim 16 wherein the microsphere, hydrogel, or microsphere-hydrogel mixture comprises a drug or therapeutic agent from about 0.1% to about 70% of the microsphere, hydrogel, or microsphere-hydrogel mixture.

18. The method of claim 1, wherein the microspheres are non-porous microspheres.

19. The method of claim 1, wherein the microspheres are made using melt encapsulation.

20. The method of claim 1, wherein the microspheres are made using oil-in-water solvent evaporation.

* * * * *

UNITED STATES PATENT AND TRADEMARK OFFICE
CERTIFICATE OF CORRECTION

PATENT NO. : 8,940,311 B2
APPLICATION NO. : 11/256416
DATED : January 27, 2015
INVENTOR(S) : Lim et al.

Page 1 of 1

It is certified that error appears in the above-identified patent and that said Letters Patent is hereby corrected as shown below:

In the Claims,

<u>Col. 19, claim 4, line 14</u>:
DELETE after about "70%"
ADD after about --50%--

<u>Col. 20, claim 17, line 50</u>:
DELETE after about "70%"
ADD after about --50%--

Signed and Sealed this
Twelfth Day of May, 2015

Michelle K. Lee
*Director of the United States Patent and Trademark Office*